(12) United States Patent
Roorda et al.

(10) Patent No.: US 7,875,285 B1
(45) Date of Patent: Jan. 25, 2011

(54) MEDICATED COATINGS FOR IMPLANTABLE MEDICAL DEVICES HAVING CONTROLLED RATE OF RELEASE

(75) Inventors: Wouter E. Roorda, Palo Alto, CA (US); Ni Ding, San Jose, CA (US); Stephen D. Pacetti, San Jose, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 973 days.

(21) Appl. No.: 10/619,727

(22) Filed: Jul. 15, 2003

(51) Int. Cl.
  *A61F 2/02* (2006.01)
(52) U.S. Cl. .................................................... 424/425
(58) Field of Classification Search ....................... None
  See application file for complete search history.

(56) References Cited

U.S. PATENT DOCUMENTS

| | | | |
|---|---|---|---|
| 4,733,665 A | 3/1988 | Palmaz | 128/343 |
| 4,800,882 A | 1/1989 | Gianturco | 128/343 |
| 4,886,062 A | 12/1989 | Wiktor | 127/343 |
| 4,977,901 A | 12/1990 | Ofstead | 128/772 |
| 5,112,457 A | 5/1992 | Marchant | 204/165 |
| 5,328,471 A | 7/1994 | Slepian | 604/101 |
| 5,455,040 A | 10/1995 | Marchant | 424/426 |
| 5,464,650 A | 11/1995 | Berg et al. | 427/2.3 |
| 5,578,073 A | 11/1996 | Haimovich et al. | 623/1 |
| 5,605,696 A | 2/1997 | Eury et al. | 424/423 |
| 5,667,767 A | 9/1997 | Greff et al. | 424/9.411 |
| 5,670,558 A | 9/1997 | Onishi et al. | 523/112 |
| 5,700,286 A | 12/1997 | Tartaglia et al. | 623/1 |
| 5,716,981 A | 2/1998 | Hunter et al. | 514/449 |
| 5,824,049 A | 10/1998 | Ragheb et al. | 623/1 |
| 5,830,178 A | 11/1998 | Jones et al. | 604/49 |
| 5,837,313 A | 11/1998 | Ding et al. | 427/2.21 |
| 5,851,508 A | 12/1998 | Greff et al. | 424/9.411 |
| 5,858,746 A | 1/1999 | Hubbell et al. | 435/177 |
| 5,865,814 A | 2/1999 | Tuch | 604/265 |
| 5,873,904 A | 2/1999 | Ragheb et al. | 623/1 |
| 5,971,954 A | 10/1999 | Conway et al. | 604/96 |
| 5,980,928 A | 11/1999 | Terry | 424/427 |
| 5,980,972 A | 11/1999 | Ding | 427/ 2.24 |
| 6,015,541 A | 1/2000 | Greff et al. | 424/1.25 |
| 6,042,875 A | 3/2000 | Ding et al. | 427/2.24 |
| 6,051,648 A | 4/2000 | Rhee et al. | 525/54.1 |
| 6,056,993 A | 5/2000 | Leidner et al. | 427/2.25 |
| 6,060,451 A | 5/2000 | DiMaio et al. | 514/13 |
| 6,080,488 A | 6/2000 | Hostettler et al. | 428/423.3 |
| 6,096,070 A | 8/2000 | Ragheb et al. | 623/1 |
| 6,099,562 A | 8/2000 | Ding et al. | 623/1.46 |
| 6,110,188 A | 8/2000 | Narciso, Jr. | 606/153 |
| 6,113,629 A | 9/2000 | Ken | 623/1.1 |
| 6,120,536 A | 9/2000 | Ding et al. | 623/1.43 |
| 6,120,904 A | 9/2000 | Hostettler et al. | 428/423.3 |
| 6,121,027 A | 9/2000 | Clapper et al. | 435/180 |
| 6,129,761 A | 10/2000 | Hubbell | 623/11 |
| 6,153,252 A | 11/2000 | Hossainy et al. | 427/2.3 |
| 6,165,212 A | 12/2000 | Dereume et al. | 623/1.13 |

FOREIGN PATENT DOCUMENTS

| | | |
|---|---|---|
| EP | 0 665 023 | 8/1995 |
| EP | 0 970 711 | 1/2000 |
| EP | 0 970 711 A2 * | 12/2000 |
| WO | WO 00/12147 | 3/2000 |
| WO | WO 00/64506 | 11/2000 |
| WO | WO 01/01890 | 1/2001 |

\* cited by examiner

*Primary Examiner*—Carlos A Azpuru
(74) *Attorney, Agent, or Firm*—Squire, Sanders & Dempsey L.L.P.

(57) ABSTRACT

A coating for a medical device, particularly for a drug eluting stent, is described. The coating can include a polymer having in a dry state a glass transition temperature within a range of between about 20° C. and about 55° C.

18 Claims, No Drawings

MEDICATED COATINGS FOR IMPLANTABLE MEDICAL DEVICES HAVING CONTROLLED RATE OF RELEASE

BACKGROUND

1. Field of the Invention

This invention is directed to coatings for implantable medical devices, such as drug eluting vascular stents.

2. Description of the State of the Art

Percutaneous transluminal coronary angioplasty (PTCA) is a procedure for treating heart disease. A catheter assembly having a balloon portion is introduced percutaneously into the cardiovascular system of a patient via the brachial or femoral artery. The catheter assembly is advanced through the coronary vasculature until the balloon portion is positioned across the occlusive lesion. Once in position across the lesion, the balloon is inflated to a predetermined size to radially compress against the atherosclerotic plaque of the lesion to remodel the lumen wall. The balloon is then deflated to a smaller profile to allow the catheter to be withdrawn from the patient's vasculature.

A problem associated with the above procedure includes formation of intimal flaps or torn arterial linings which can collapse and occlude the conduit after the balloon is deflated. Moreover, thrombosis and restenosis of the artery may develop over several months after the procedure, which may require another angioplasty procedure or a surgical by-pass operation. To reduce the partial or total occlusion of the artery by the collapse of arterial lining and to reduce the chance of the development of thrombosis and restenosis, a stent is implanted in the lumen to maintain the vascular patency.

Stents are used not only as a mechanical intervention but also as a vehicle for providing biological therapy. As a mechanical intervention, stents act as scaffoldings, functioning to physically hold open and, if desired, to expand the wall of the passageway. Typically, stents are capable of being compressed, so that they can be inserted through small vessels via catheters, and then expanded to a larger diameter once they are at the desired location. Examples in patent literature disclosing stents which have been applied in PTCA procedures include stents illustrated in U.S. Pat. No. 4,733,665 issued to Palmaz, U.S. Pat. No. 4,800,882 issued to Gianturco, and U.S. Pat. No. 4,886,062 issued to Wiktor.

Biological therapy can be achieved by medicating the stents. Medicated stents provide for the local administration of a therapeutic substance at the diseased site. In order to provide an efficacious concentration to the treated site, systemic administration of such medication often produces adverse or toxic side effects for the patient. Local delivery is a preferred method of treatment in that smaller total levels of medication are administered in comparison to systemic dosages, but are concentrated at a specific site. Local delivery thus produces fewer side effects and achieves more favorable results. One proposed method for medicating stents involves the use of a polymeric carrier coated onto the surface of a stent. A solution which includes a solvent, a polymer dissolved in the solvent, and a therapeutic substance dispersed in the blend is applied to the stent. The solvent is allowed to evaporate, leaving on the stent surface a coating of the polymer and the therapeutic substance impregnated in the polymer. The embodiments of the invention provide coatings for implantable devices, such as stents, and methods of coating the same.

SUMMARY

A coating for an implantable medical device is provided, the coating comprising a first region having a drug incorporated therein, and a second region disposed over the first region, wherein the second region comprises a polymer for modifying the rate of release of the drug, the polymer having in a dry state a glass transition temperature within a range of between about 35° C. and about 50° C., wherein the polymer in the dry state contains less than about 1 mass % of water. The polymer can be acrylic or non-acrylic homo-, co-, or terpolymer.

A coating for an implantable medical device is provided, the coating comprises a polymer and a drug incorporated therein, wherein a glass transition temperature of the polymer is the temperature that allows the morphology of the polymer to change the release rate of the drug when a body temperature of the patient in which the device has been implanted rises to a temperature above the patient's normal body temperature.

A method of coating an implantable medical device is provided, the method comprises depositing a first layer on the device, the first layer including a drug incorporated therein, and depositing a second layer over the first layer, the second layer comprising a polymer for modifying the rate of release of the drug, wherein the polymer has a glass transition temperature in a dry state within a range of between about 35° C. and about 50° C., wherein the polymer in the dry state contains less than about 1 mass % of water.

DETAILED DESCRIPTION

A coating for an implantable medical device, such as a stent, according to one embodiment of the present invention, can include an optional primer layer, a drug-polymer layer, and a topcoat layer. The drug-polymer layer can be applied directly onto the stent surface to serve as a reservoir for an active agent or a drug which is incorporated into the drug-polymer layer. The primer layer can be applied between the stent and the drug-polymer layer to improve the adhesion of the drug-polymer layer to the stent. The topcoat layer, which can be essentially free from any therapeutic substances or drugs, serves as a rate limiting membrane controlling the rate of release of the drug. During the formation of the topcoat layer, a quantity of drug, however small, can migrate into the topcoat layer from the drug-polymer layer.

While typically it is beneficial to decrease the rate of release of the drug, sometimes it is desirable to increase the rate of drug release. For example, if a localized inflammation develops, it may be necessary to accelerate the rate of release of anti-inflammatory drugs such as β-estradiol or clobetasol to fight the inflammatory reaction. When the drugs have suppressed the inflammation, it is desirable to have the stent coating return to a condition when the rate of drug release is slow again.

The rate of release of the drug through the polymer, such as the topcoat membrane, is related to the rate of diffusion of the drug through the matrix. The rate of diffusion is in turn related to the water adsorption rate, the degree of crystallinity, if any, and the glass transition temperature ($T_g$) of the polymer. When an amorphous or semi-crystalline polymer is exposed to an increasing temperature, both the coefficient of expansion and the heat capacity of the polymer increase as the temperature is raised, indicating increased molecular motion. The $T_g$ is defined as a temperature approximately in the middle of the temperature region where the onset of segmental motion in the chains of the polymer occurs leading to the eventual transition of the polymer from a glassy solid to an amorphous solid at atmospheric pressure. In other words, the $T_g$ is defined as an average temperature in the temperature region at which an amorphous polymer (or the amorphous regions in a partially crystalline polymer) changes from a hard and relatively brittle condition to a viscoelastic (rubbery) condition.

It is known in the art that the $T_g$ of a polymer may depend on a method of measuring the $T_g$. For the purposes of the present invention, the $T_g$ for all polymers discussed below have been determined using the method of differential scanning calorimetry (DSC). DSC measures the change in heat capacity of a semicrystalline polymer as the polymer is exposed to an increasing temperature. Also, it has to be kept in mind that some hydrophilic polymers having a relatively high $T_g$ (e.g., about 50° C. or higher) when in a dry state, may have significantly lower $T_g$ in the aqueous environment such as inside the patient's body. This phenomenon may be caused by the fact that when the hydrophilic polymer is placed in contact with the body fluids (e.g., blood), the polymer can absorb water which serves as plasticizer leading to substantial reduction of the polymer's $T_g$. The term "dry state" is defined as a condition of a polymer when the polymer contains less than about 1 mass % of water at equilibrium, at ambient conditions. To illustrate, polymers capable of absorbing at least 1% of water (as a percentage of the polymer's weight), at room temperature and ambient pressure, can have their $T_g$ substantially lowered when the polymer is exposed to the aqueous environment than when the polymer is dry. For example, the $T_g$ of dry poly(ethylene-co-vinyl alcohol) (also known as EVAL™) is about 55° C. (328° K.), and the $T_g$ of poly(D,L-lactide) is about 50° C. (323° K.). However, EVAL is capable of absorbing maximum about 5% of water, and poly(D,L-lactide) is capable of absorbing maximum about 1% of water at ambient temperature and pressure. The $T_g$ of both EVAL and poly(D,L-lactide) which absorbed the maximum amount of water they are capable of absorbing is within the range of between about 35° C. (308° K.) and about 42° C. (315° K.) range. Thus, the $T_g$ of such and similar hydrophilic polymers can be lower by as much as 20 degrees after the polymer has absorbed the maximum amount of water.

According to one embodiment of the present invention, the drug-polymer layer or the topcoat layer of the stent coating can be fabricated of a homopolymer, a copolymer or a terpolymer that can have the preferred $T_g$ in a dry state (1) between about 20° C. (293° K.) and about 55° C. (328° K.); (2) between about 35° C. (308° K.) and about 50° C. (323° K.); (3) between about 37° C. (310° K.) and about 50° C. (323° K.); (4) between about 37° C. (310° K.) and about 40° C. (313° K.); or (5) about 37° C. (310° K.).

According to another embodiment of the present invention, the $T_g$ of the polymer forming the topcoat layer is greater than, or equal to, the $T_g$ of the polymer forming the drug-polymer layer. Yet in another embodiment, the $T_g$ of the polymer forming the topcoat layer can be less than the $T_g$ of the polymer forming the drug-polymer layer. In yet another embodiment, the $T_g$ of the polymer forming at least one of the drug-polymer and the topcoat layers is within the preferred ranges described above, while the $T_g$ of the polymer forming the other layer is outside the ranges. For example, the topcoat layer can be formed of a polymer having a $T_g$ within any of the previously described ranges (e.g., 37-40° C.), while the polymer forming the drug-polymer layer can have a $T_g$ above 50° C., e.g., 55° C. Yet in another example, the drug-polymer layer can be formed of a polymer having a $T_g$ within any of the previously described ranges (e.g., 37-40° C.), while the polymer forming the topcoat layer can have a $T_g$ above 50° C., e.g., 55° C.

For polymers forming, for example, a topcoat layer and having a $T_g$ of at least 35-37° C., when the temperature of the patient increases above normal body temperature and reaches at least the $T_g$ of the polymer, the morphology of the polymer changes to a more rubbery consistency, which allows for an increased rate of release of the drug. When the temperature of the patient falls below the polymer's $T_g$, the polymer becomes hard again which results in the reduction of the rate of release of the drug.

According to one embodiment of the present invention, a coating for an implantable medical device comprises a first region having a drug incorporated therein and a second region disposed over the first region, wherein the second region comprises a polymer for modifying the rate of release of the drug, the polymer having in a dry state a glass transition temperature within a range of between about 35° C. and about 50° C., wherein the polymer in the dry state contains less than about 1 mass % of water. The coating may also have the polymer with a melting temperature above about 50° C., and may additionally includes a substance having the melting temperature within the range between about 32° C. and 40° C.

According to another embodiment of the present invention, a method of coating an implantable medical device comprises depositing a first layer on the device, the first layer including a drug incorporated therein, and depositing a second layer over the first layer, the second layer comprising a polymer for modifying the rate of release of the drug, wherein the polymer has a glass transition temperature in a dry state within a range of between about 35° C. and about 50° C., wherein the polymer in the dry state contains less than about 1 mass % of water. The method may also have the polymer with a melting temperature above about 50° C., and may additionally include a substance having the melting temperature within the range between about 32° C. and 40° C.

Examples of suitable polymers that can be used for making the stent coatings include polymers having the general formula (I)

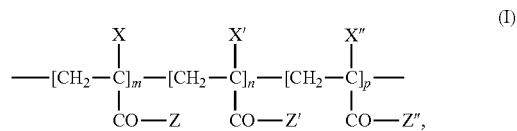

wherein:

X, X', and X" is each, independently, a hydrogen atom or an alkyl group, such as methyl or ethyl group;

Z, Z', and Z" is each, independently, a substituted or unsubstituted amino group or an alkoxy group OR, OR', and OR", where R, R' and R" is each, independently, a $C_1$ to $C_{12}$ straight chained or branched aliphatic radical; and "m," "n," and "p" is each an integer, where m>0, n≧0, and p≧0. If both n=0 and p=0, the polymer of formula (I) is a homopolymer (i.e., PBMA). If only one of "n" and "p" is 0, the polymer of formula (I) is a copolymer, and if both n>0 and p>0, the polymer of formula (I) is a terpolymer.

Polymers of formula (I) can be used for making the optional primer layer, the drug-polymer layer, the topcoat membrane, or any combination thereof. The polymers of formula (I) or their blends are herein referred to as "acrylic polymers," the term inclusive of homopolymers, copolymers, terpolymers, oligomers and prepolymers derived from monomers having the acrylic or methacrylic group $CH_2=C(X)—CO—$. The acrylic polymers within the scope of the present invention include polymers with Z, Z', and Z" being an alkoxy group ("polyacrylates") and polymers with Z, Z', and Z" being an amino group ("polyacrylamides").

One example of a of polymer, described by formula (I), that can be used for fabricating the drug-polymer layer and/or the topcoat membrane is poly(n-propyl methacrylate) (PPMA) where in formula (I) $X=CH_3$, n=0, p=0, and Z is n-propoxy group $OC_3H_7$. PPMA has $T_g$ of about 35° C. (308° K.). Alternatively, other suitable polyacrylates or polyacrylamides described by formula (I) can be used, some examples of which are summarized in Table 1.

TABLE 1

Examples of polyacrylates or polyacrylamides

| No. | Polymer | $T_g$, ° K. |
|---|---|---|
| 1 | Poly(tert-butyl acrylate) | 316 |
| 2 | Poly[3-chloro-2,2-bis(chloromethyl)propyl acrylate] | 319 |
| 3 | Poly(cyanobenzyl acrylate) | 317 |
| 4 | Poly(2-ethoxycarbonylphenyl acrylate) | 303 |
| 5 | Poly(2-methoxycarbonylphenyl acrylate) | 319 |
| 6 | Poly(3-methoxycarbonylphenyl acrylate) | 311 |
| 7 | Poly(4-methoxyphenyl acrylate) | 324 |
| 8 | Poly(3-ethoxycarbonylphenyl acrylate) | 297 |
| 9 | Poly(4-ethoxycarbonylphenyl acrylate) | 310 |
| 10 | Poly(hexadecyl acrylate) | 308 |
| 11 | Poly(methyl acrylate), head-to-head | 304 |
| 12 | Poly(methyl acrylate), head-to-tail | 278 |
| 13 | Poly(3-dimethylaminophenyl acrylate) | 320 |
| 14 | Poly(neopentyl acrylate) | 295 |
| 15 | Poly(tetradecyl acrylate) | 297 |
| 16 | Poly(m-tolyl acrylate) | 298 |
| 17 | Poly(o-tolyl acrylate) | 325 |
| 18 | Poly(p-tolyl acrylate) | 316 |
| 19 | Poly(n-butyl acrylamide) | 319 |
| 20 | Poly(iso-decyl acrylamide) | 313 |
| 21 | Poly(n-butyl methacrylate) | 298 |
| 22 | Poly(iso-butyl methacrylate) | 326 |
| 23 | Poly(cyclohexyl methacrylate), isotactic | 324 |
| 24 | Poly(1H,1H,5H-octafluoropentyl methacrylate) | 309 |
| 25 | Poly(iso-propyl methacrylate), isotactic | 300 |
| 26 | Poly(3,3-dimethylbutyl methacrylate) | 318 |
| 27 | PMMA, isotactic | 311 |
| 28 | Poly(phenylethyl methacrylate) | 299 |
| 29 | Poly(n-propyl methacrylate) | 308 |
| 30 | Poly(ethyl chloroacrylate), isotactic | 308 |
| 32 | Poly(ethyl methacrylate) | 300 |
| 33 | Poly(ethyl fluoromethacrylate) | 316 |

In addition to homopolymers disclosed in Table 1, in some embodiments of the present invention, copolymers or terpolymers described by formula (I) can be used, for example, copolymers or terpolymers having units derived from n-butyl methacrylate. For a copolymer or a terpolymer, the $T_g$ (on the Kelvin scale) is generally the mass fraction-weighted average of the constituent components of the copolymer. Consequently, a copolymer or terpolymer of formula (I) with predetermined higher or lower value of $T_g$ can be used. For example, poly(methyl methacrylate-co-n-butyl methacrylate) [P(MMA-BMA)] having about 15 molar % of units derived from methyl methacrylate and about 85 molar % of units derived from n-butyl methacrylate can be used. Such P(MMA-BMA) copolymer is described by formula (I) where $X=X'=CH_3$; $Z=OCH_3$, $Z'=OC_4H_9$; the m:n ratio is 1:5.67, and p=0, and the copolymer's $T_g$ is about 37° C. (310° K.). Another example of an acceptable copolymer is poly(n-butyl methacrylate-co-iso-butyl methacrylate) [P(n-BMA-1-BMA)] having about equimolar amount of units derived from n-butyl methacrylate- and -iso-butyl methacrylate. Such P(n-BMA-1-BMA) copolymer is described by formula (I) where $X=X'=CH_3$; $Z=On-C_4H_9$, $Z'=Oiso-C_4H_9$; the m:n ratio is 1:1, and p=0, and the copolymer's $T_g$ is about 39° C. (312° K.).

According to other embodiments of the present invention, some non-acrylic polymers can be also used for making the stent coating. The term "non-acrylic polymers" refers to polymers that are free of units derived from monomers having acrylic groups. The term "non-acrylic polymers" is used as inclusive of non-acrylic homopolymers, copolymers, terpolymers, oligomers and prepolymers. Non-acrylic polymers that can be used can be obtained by polymerization of ethylenically unsaturated compounds such as olefins or vinyl compounds. Suitable non-acrylic polymers can have $T_g$ values within the previously described ranges. Table 2 includes some examples of non-acrylic polymers that can be used.

TABLE 2

Examples of non-acrylic polymers

| No. | Polymer | $T_g$, ° K. |
|---|---|---|
| 1 | Poly(4-methoxycarbonyl-3-methyl-1-butenylene) | 326 |
| 2 | Poly(2-cyclohexylethylethylene) | 313 |
| 3 | Poly(hexadecylethylene) | 328 |
| 4 | Poly(iso-butylethylene) | 302 |
| 5 | Poly(iso-propylethylene), atactic | 323 |
| 6 | Poly(3,3-dimethylbutylethylene) | 326 |
| 7 | Poly(1,1,2-trimethylethylene) | 310 |
| 8 | Poly(4,4 dimethylpentylethylene) | 313 |
| 9 | Poly(propyl-2propylene) | 300 |
| 10 | Poly(2,2,2-trifluoroethoxytrifluoroethylene) | 308 |
| 11 | Poly(4-methoxybenzoylethylene) | 319 |
| 12 | Poly(3,4-dimethoxybenzoylethylene) | 315 |
| 13 | Poly(vinyl fluoride) | 314 |
| 14 | Poly(vinyl acetate) | 305 |
| 15 | Poly(ethylene-co-vinyl alcohol)(EVAL) | 328 |
| 16 | Poly(cyclopentanoyloxyethylene) | 309 |
| 17 | Poly(formyloxyethylene), 60% syndiotactic | 310 |
| 18 | Poly(formyloxyethylene), 50% syndiotactic | 306 |
| 19 | Poly(4-(sec-butoxymethyl) styrene) | 313 |
| 20 | Poly(4-butoxystyrene) | 320 |
| 21 | Poly(3-ethylstyrene) | 303 |

In some embodiments of the present invention, instead of individual polymers, blends of polymers can be used for fabricating the drug-polymer layer and/or the topcoat membrane, as long as the blend has $T_g$ within the previously described ranges. The blends can include polyacrylate(s) or polyacrylamide(s) described by formula (I), and/or non-acrylic polymer(s), including both non-acrylic polymers included in Table 2 and other non-acrylic polymers, or any combination thereof.

Examples of polyacrylates that can be included in the polymer blends include poly(n-butyl methacrylate) (PBMA), poly(methyl methacrylate) (PMMA), and poly(iso-butyl methacrylate) (PiBMA), all described by formula (I), where $X=CH_3$, n=0, p=0, and Z is, respectively, $On-C_4H_9$, $OCH_3$, and $Oiso-C_4H_9$.

Examples of polyacrylate-only blends include a blend of PBMA and PMMA, the blend containing about 85 mass % of PBMA and the balance PMMA, and a blend of PBMA and PiBMA, the blend containing about 57 mass % of PBMA and the balance PiBMA. Polymer blends also include blends of homopolymer(s) and co- or terpolymer(s), such as a blend of about 50 mass % of PMMA and the balance P(MMA-BMA), having about 58 molar % of units derived from butyl methacrylate and about 42 molar % from methyl methacrylate.

According to one embodiment, if a polymer blend is used to make the topcoat layer, a two-phase composition can be utilized. The first phase can include a first polymer having the melting temperature ($T_m$) above about 40° C., for example, above about 65° C. The second phase can include a material, which can be a monomer, an oligomer or a polymer, which is immiscible with the polymer forming the first phase and which has $T_n$, within the range between about 32° C. and 40° C., for example, about 37° C. The $T_m$ of a polymer is defined as the temperature at which the last trace of crystallinity in a polymer disappears as a sample is exposed to increasing heat. For a given polymer, the $T_m$ is always greater than the $T_g$. The $T_m$ of a monomer or an oligomer is defined as the temperature at which the monomer or oligomer is fluid at ambient pressure.

The mass ratio between the polymer forming the first and the second phase can be between about 1:3 and about 1:19, such as between about 1:4 and about 1:10, for example, about 1:5. Such composition can form two distinct phases within the topcoat layer. When the body temperature rises to above its normal temperature of about 37° C., the second polymer can melt leading to an increase in the rate of release of the drug. Examples of some compositions that can be used to make the two-phase topcoat layer described above can be illustrated as shown in Table 3.

TABLE 3

Examples of compositions forming two-phase topcoat layers.

| No. | First phase Polymer | $T_m$, ° C. | Second phase Substance | $T_m$, ° C. | Mass ratio between the first and the second phases |
|---|---|---|---|---|---|
| 1 | Poly(vinylidene fluoride-co-hexafluoropropene) | 135 | 1-tetra-decanol | 39 | 1:9 |
| 2 | Poly(ethylene-co-vinyl alcohol), 44 mol. % vinyl alcohol-derived units | 155 | Vegetable wax | 40 | 1:5 |
| 3 | Poly(ethylene-co-vinyl acetate), 25 mol. % vinyl acetate-derived units | 78 | Cocoa butter | 32 | 1:19 |
| 4 | Poly(vinylidene fluoride) | 67 | Tri-glyceride (stearin-di-palmityl) | 36 | 1:3 |

To fabricate the coating, one of the polyacrylates or polyacrylamides, or non-acrylate polymers, or a blend thereof described above can be applied on the stent using commonly used techniques known to those having ordinary skill in the art. For example, the polyacrylate can be applied to the stent by dissolving the polymer in a solvent, or a mixture of solvents, and applying the resulting solution on the stent by spraying or immersing the stent in the solution.

Representative examples of some solvents include N,N-dimethylacetamide (DMAC), N,N-dimethylformamide (DMF), tethrahydrofurane (THF), cyclohexanone, xylene, toluene, acetone, methyl ethyl ketone, propylene glycol monomethyl ether, methyl butyl ketone, ethyl acetate, n-butyl acetate, and dioxane. Examples of mixtures of solvents include mixtures of DMAC and methanol (e.g., a 50:50 by mass mixture), cyclohexanone and acetone (e.g., 80:20, 50:50, 20:80 by mass mixtures), acetone and xylene (e.g. a 50:50 by mass mixture), and acetone, FLUX REMOVER AMS™, and xylene (e.g., a 10:50:40 by mass mixture). FLUX REMOVER AMS is the trade name of a solvent manufactured by Tech Spray, Inc. of Amarillo, Tex. comprising about 93.7% of a mixture of 3,3-dichloro-1,1,1,2,2-pentafluoropropane and 1,3-dichloro-1,1,2,2,3-pentafluoropropane, and the balance methanol, with trace amounts of nitromethane.

At least one of the drug-polymer layer or the topcoat layer must have $T_g$ that falls within the previously described ranges. However, other polymers can also be used for the primer, drug-polymer and/or topcoat layers so long as the polymer or a polymer blend forming either the drug-polymer layer or the topcoat layer can have the $T_g$ within the specified ranges.

Representative examples of alternative polymers that can be used be used for making the primer, drug-polymer and/or topcoat layers include poly(hydroxyvalerate), poly(L-lactic acid), polycaprolactone, poly(lactide-co-glycolide), poly(hydroxybutyrate), poly(hydroxybutyrate-co-valerate), polydioxanone, polyorthoester, polyanhydride, poly(glycolic acid), poly(D,L-lactic acid), poly(glycolic acid-co-trimethylene carbonate), polyphosphoester, polyphosphoester urethane; poly(amino acids), polycyanoacrylates, poly(trimethylene carbonate), poly(iminocarbonate), co-poly(ether-esters), polyalkylene oxalates, polyphosphazenes, biomolecules (such as fibrin, fibrinogen, cellulose, starch, collagen and hyaluronic acid), polyurethanes, silicones, polyesters, polyolefins, polyisobutylene and ethylene-alphaolefin copolymers, polyvinyl chloride, polyvinyl ethers (such as polyvinyl methyl ether), polyvinylidene halides (such as polyvinylidene fluoride and polyvinylidene chloride), polyacrylonitrile, polyvinyl ketones, polyvinyl aromatics (such as polystyrene), polyvinyl esters, acrylonitrile-styrene copolymers, ABS resins, ethylene-vinyl acetate copolymers, polyamides (such as Nylon 66 and polycaprolactam), alkyd resins, polycarbonates, polyoxymethylenes, polyimides, polyethers, epoxy resins, polyurethanes, rayon, rayon-triacetate, cellulose, cellulose acetate, cellulose butyrate, cellulose acetate butyrate, cellophane, cellulose nitrate, cellulose propionate, cellulose ethers, and carboxymethyl cellulose.

The coating of the present invention has been described in conjunction with a stent. However, the coating can also be used with a variety of other medical devices. Examples of the implantable medical device, that can be used in conjunction with the embodiments of this invention include stent-grafts, grafts (e.g., aortic grafts), artificial heart valves, cerebrospinal fluid shunts, pacemaker electrodes, axius coronary shunts and endocardial leads (e.g., FINELINE and ENDOTAK, available from Guidant Corporation). The underlying structure of the device can be of virtually any design. The device can be made of a metallic material or an alloy such as, but not limited to, cobalt-chromium alloys (e.g., ELGILOY), stainless steel (316L), "MP35N," "MP20N," ELASTINITE (Nitinol), tantalum, tantalum-based alloys, nickel-titanium alloy, platinum, platinum-based alloys such as, e.g., platinum-iridium alloy, iridium, gold, magnesium, titanium, titanium-based alloys, zirconium-based alloys, or combinations thereof. Devices made from bioabsorbable or biostable polymers can also be used with the embodiments of the present invention.

"MP35N" and "MP20N" are trade names for alloys of cobalt, nickel, chromium and molybdenum available from Standard Press Steel Co. of Jenkintown, Pa. "MP35N" consists of 35% cobalt, 35% nickel, 20% chromium, and 10% molybdenum. "MP20N" consists of 50% cobalt, 20% nickel, 20% chromium, and 10% molybdenum.

The active agent, therapeutic substance or drug, the terms which are used interchangeably, can include any substance capable of exerting a therapeutic or prophylactic effect for a patient. The drug may include small molecule drugs, peptides, proteins, oligonucleotides, and the like. The drug could be designed, for example, to inhibit the activity of vascular smooth muscle cells. It can be directed at inhibiting abnormal or inappropriate migration and/or proliferation of smooth muscle cells to inhibit restenosis.

Examples of drugs include antiproliferative substances such as actinomycin D, or derivatives and analogs thereof (manufactured by Sigma-Aldrich of Milwaukee, Wis., or COSMEGEN available from Merck). Synonyms of actinomycin D include dactinomycin, actinomycin IV, actinomycin $I_1$, actinomycin $X_1$, and actinomycin $C_1$. The active agent can also fall under the genus of antineoplastic, anti-inflammatory, antiplatelet, anticoagulant, antifibrin, antithrombin, antimitotic, antibiotic, antiallergic and antioxidant substances. Examples of such antineoplastics and/or antimitotics include paclitaxel (e.g. TAXOL® by Bristol-Myers Squibb Co., Stamford, Conn.), docetaxel (e.g. TAXOTERE®, from Aventis S.A., Frankfurt, Germany) methotrexate, azathioprine, vincristine, vinblastine, fluorouracil, doxorubicin hydrochloride (e.g. ADRIAMYCIN® from Pharmacia & Upjohn, Peapack N.J.), and mitomycin (e.g. MUTAMYCIN® from Bristol-Myers Squibb Co., Stamford, Conn.). Examples of such antiplatelets, anticoagulants, antifibrin, and antithrombins include sodium heparin, low molecular weight heparins, heparinoids, hirudin, argatroban, forskolin, vapiprost, prostacyclin and prostacyclin analogues, dextran, D-phe-pro-arg-chloromethylketone (synthetic antithrombin), dipyridamole, glycoprotein IIb/IIIa platelet membrane receptor antagonist antibody, recombinant hirudin, and thrombin inhibitors such as ANGIOMAX™ (Biogen, Inc., Cambridge, Mass.). Examples of such cytostatic or antiproliferative agents include angiopeptin, angiotensin converting enzyme inhibitors such as captopril (e.g. CAPOTEN® and CAPOZIDE® from Bristol-Myers Squibb Co., Stamford, Conn.), cilazapril or lisinopril (e.g. PRINIVIL® and PRINZIDE® from Merck & Co., Inc., Whitehouse Station, N.J.); calcium channel blockers (such as nifedipine), colchicine, fibroblast growth factor (FGF) antagonists, fish oil (omega 3-fatty acid), histamine antagonists, lovastatin (an inhibitor of HMG-CoA reductase, a cholesterol lowering drug, brand name MEVACOR® from Merck & Co., Inc., Whitehouse Station, N.J.), monoclonal antibodies (such as those specific for Platelet-Derived Growth Factor (PDGF) receptors), nitroprusside, phosphodiesterase inhibitors, prostaglandin inhibitors, suramin, serotonin blockers, steroids, thioprotease inhibitors, triazolopyrimidine (a PDGF antagonist), and nitric oxide. An example of an antiallergic agent is permirolast potassium. Other therapeutic substances or agents which may be appropriate include alpha-interferon, genetically engineered epithelial cells, tacrolimus, dexamethasone, and rapamycin and structural derivatives or functional analogs thereof, such as 40-O-(2-hydroxy)ethyl-rapamycin (known by the name of everolimus available from Novartis), 40-O-(3-hydroxy)propyl-rapamycin, 40-O-[2-(2-hydroxy)ethoxy]ethyl-rapamycin, and 40-O-tetrazole-rapamycin.

EXAMPLES

Some embodiments of the present invention are illustrated by the following examples.

Example 1

A polymer solution containing between about 0.1 mass % and about 15 mass %, for example, about 2.0 mass % of EVAL and the balance, DMAC solvent, can be prepared. The solution can be applied onto a stent to form a primer layer. To apply the primer layer, a spray apparatus, such as an EFD 780S™ spray nozzle with a VALVEMATE 7040™ control system, manufactured by EFD, Inc. of East Providence, R.I. can be used. The EFD 780S spray nozzle is an air-assisted external mixing atomizer. The composition is atomized by air and applied to the stent surfaces. During the process of applying the composition, the stent can be optionally rotated about its longitudinal axis, at a speed of 50 to about 150 rpm. The stern can also be linearly moved along the same axis during the application.

The EVAL solution can be applied to a 13-mm TETRA™ stent (available from Guidant Corporation) in a series of 10-second passes, to deposit, for example, 10 μg of coating per spray pass. Instead of the 13-mm TETRA stent, another suitable stent can be used, for example, a 12-mm VISION™ stent (also available from Guidant Corporation). Between the spray passes, the stent can be dried for about 10 seconds using flowing air with a temperature of about 60° C. Five spray passes can be applied, followed by baking the primer layer at about 140° C. for about 2 hours. As a result, a primer layer can be formed having a solids content of about 50 μg. "Solids" means the amount of the dry residue deposited on the stent after all volatile organic compounds (e.g., the solvent) have been removed.

A drug-containing formulation can be prepared comprising:

(a) between about 0.1 mass % and about 15 mass %, for example, about 2.0 mass % of EVAL;

(b) between about 0.1 mass % and about 2 mass %, for example, about 1.0 mass % of an active agent, for example, everolimus; and (c) the balance, a solvent mixture of DMAC and pentane, the solvent mixture containing about 80 mass % of DMAC and about 20 mass % of pentane.

In a manner identical to the application of the primer layer, five spray passes can be performed, followed by baking the drug-polymer layer at about 50° C. for about 2 hours, to form the drug-polymer layer having a solids content between about 30 μg and 750 μg, for example, about 90 μg, and a drug content of between about 10 μg and about 250 μg, for example, 30 μg.

Finally, a topcoat composition can be prepared, comprising:

(a) between about 1 mass % and about 10 mass %, for example, about 2 mass % of poly(methyl methacrylate-co-n-butyl methacrylate) [P(MMA-BMA)] having about 15 molar % of units derived from methyl methacrylate and about 85 molar % of units derived from n-butyl methacrylate; and (b) the balance a solvent system, for example, a solvent system including acetone and cyclohexanone in a mass ratio of about 1:1.

In a manner identical to the application of the primer layer and the drug-polymer layer, a number of spray passes are performed followed by final baking at about 50° C. for about 1 hour. As a result, the topcoat membrane can be formed, the membrane having a solids content of between about 70 μg and about 150 μg, for example, about 100 μg.

Example 2

A stent can be coated with a primer layer and a drug-polymer layer as described in Example 1. A topcoat composition can be prepared, comprising:

(a) between about 1 mass % and about 10 mass %, for example, about 2 mass % of a blend of poly(n-butyl methacrylate) (PBMA) and poly(methyl methacrylate) (PMMA), the blend containing about 85 mass % of PBMA and the balance, PMMA; and (b) the balance a solvent system, for example, a solvent system including acetone and xylene in a mass ratio of about 1:1.

In a manner identical to the application of the primer layer and the drug-polymer layer, a number of spray passes are performed followed by final baking at about 50° C. for about 1 hour. As a result, the topcoat membrane can be formed, the membrane having a solids content of between about 70 µg and about 150 µg, for example, about 100 µg.

Example 3

A stent can be coated with a primer layer and a drug-polymer layer as described in Example 1. A topcoat composition can be prepared, comprising:
(a) between about 1 mass % and about 10 mass %, for example, about 2 mass % of a blend of about 50 mass % of PMMA and the balance, P(MMA-BMA) having about 58 molar % of units derived from butyl methacrylate and about 42 molar % from methyl methacrylate; and
(b) the balance a solvent system, for example, a solvent system including acetone and cyclohexanone in a mass ratio of about 1:1.

In a manner identical to the application of the primer layer and the drug-polymer layer, a number of spray passes are performed followed by final baking at about 50° C. for about 1 hour. As a result, the topcoat membrane can be formed, the membrane having a solids content of between about 70 µg and about 150 µg, for example, about 100 µg.

Example 4

A stent can be coated with a primer layer and a drug-polymer layer as described in Example 1. A topcoat composition can be prepared, comprising:
(a) between about 1 mass % and about 10 mass %, for example, about 2 mass % of a poly(formyloxyethylene) which is about 50% syndiotactic; and
(b) the balance a solvent system, for example, a solvent system including acetone and DMAC in a mass ratio of about 1:1.

In a manner identical to the application of the primer layer and the drug-polymer layer, a number of spray passes are performed followed by final baking at about 60° C. for about 1 hour. As a result, the topcoat membrane can be formed, the membrane having a solids content of between about 70 µg and about 120 µg, for example, about 100 µg.

Example 5

A stent can be coated with a primer layer and a drug-polymer layer as described in Example 1. A topcoat composition can be prepared, comprising:
(a) between about 1 mass % and about 10 mass %, for example, about 2 mass % of a blend of PBMA and poly(iso-butyl methacrylate), the blend containing about 57 mass % of PBMA and the balance, poly(iso-butyl methacrylate); and
(b) the balance a solvent system, for example, a solvent system including acetone and xylene in a mass ratio of about 1:1.

In a manner identical to the application of the primer layer and the drug-polymer layer, a number of spray passes are performed followed by final baking at about 50° C. for about 1 hour. As a result, the topcoat membrane can be formed, the membrane having a solids content of between about 70 µg and about 120 µg, for example, about 100 µg.

Example 6

A stent was coated with a primer layer as described in Example 1. A drug-containing formulation was prepared comprising:
(a) about 2.0 mass % of EVAL;
(b) about 1.0 mass % of estradiol; and
(c) the balance, DMAC solvent.

In a manner identical to the application of the primer layer, the drug-containing formulation was sprayed over the dry primer layer, followed by baking at about 60° C. for about 2 hours, to form the drug-polymer layer having a content of estradiol of about 240 µg.

A topcoat composition was prepared, comprising:
(a) about 2 mass % PBMA; and
(b) the balance a solvent system including acetone, FLUX REMOVER AMS, and xylene in a mass ratio between acetone, FLUX REMOVER AMS, and xylene of about 1:5:4.

In a manner identical to the application of the primer layer and the drug-polymer layer, the topcoat formulation was sprayed over the dry drug-polymer layer followed by final baking at about 50° C. for about 1 hour. As a result, the topcoat membrane was formed, the membrane having a solids content of about 50 µg.

The stent coating made as described above was then tested for drug release. The stent was immersed in an aqueous solution of poly(ethylene glycol) having molecular weight of about 4,000, the solution was heated to about 37° C., and the drug release was measured by the HPLC method every 10 minutes for about 260 minutes while the temperature of the solution was maintained constant at about 37° C. The drug release rate was practically constant and the average release rate was about 1.53 µg per hour.

After about 260 minutes at about 37° C., the solution was heated to about 41° C., and the drug release was measured by the HPLC method every 10 minutes for about 500 minutes while the temperature of the solution was maintained constant at about 41° C. The drug release rate was practically constant and the average release rate was about 2.5 µg per hour.

After about 500 minutes at about 41° C., the solution was cooled to about 37° C., and the drug release was measured by the HPLC method every 10 minutes for about 705 minutes while the temperature of the solution was maintained constant at about 37° C. The drug release rate was practically constant and the average release rate was about 1.5 µg per hour.

After about 705 minutes at about 37° C., the solution was again heated to about 41° C., and the drug release was measured by the HPLC method every 10 minutes for about 690 minutes while the temperature of the solution was maintained constant at about 41° C. The drug release rate was practically constant and the average release rate was about 2.3 µg per hour.

Finally, after about 690 minutes at about 41° C., the solution once again was cooled to about 37° C., and the drug release was measured by the HPLC method every 10 minutes for about 665 minutes while the temperature of the solution was maintained constant at about 37° C. The drug release rate was again practically constant and the average release rate was about 1.1 µg per hour.

On the average, the release rate increased by about 60% each time the temperature was raised from about 37° C. to about 41° C.

While particular embodiments of the present invention have been shown and described, it will be obvious to those skilled in the art that changes and modifications can be made without departing from this invention in its broader aspects. Therefore, the appended claims are to encompass within their scope all such changes and modifications as fall within the true spirit and scope of this invention.

What is claimed is:

1. A coating for an implantable medical device, the coating comprising a first region comprising a polymer and a drug incorporated therein and a second region disposed over the first region,
wherein the second region comprises a polymer and a material having a melting temperature within the range between about 32° C. and 40° C. for modifying the rate of release of the drug, the polymer in the second region having in a dry state a glass transition temperature within a range of about 35° C. and about 50° C., wherein the polymer in the second region in the dry state contains less than about 1 mass % of water, and wherein when the body temperature of a patient in which the implantable medical device comprising the coating is implanted rises to a temperature above the patient's normal body temperature, the morphology of the coating changes so as to change the release rate of the drug in the coating.

2. The coating of claim 1, wherein the implantable medical device is a stent.

3. The coating of claim 1, wherein the drug is an anti-inflammatory drug.

4. The coating of claim 1, wherein the polymer in the second region, the polymer in the first region, or both polymers in the first and the second regions comprise an acrylic polymer, a non-acrylic polymer, or blends thereof.

5. The coating of claim 4, wherein the non-acrylic polymer is selected from the group consisting of poly(2-cyclohexylethylethylene), atactic poly(isopropylethylene), poly(1,1,2-trimethylethylene), poly(4,4 dimethylpentylethylene), poly(2,2,2-trifluoroethoxytrifluoroethylene), poly(4-methoxybenzoylethylene), poly(3,4-dimethoxybenzoylethylene), poly(vinyl fluoride), poly(cyclopentanoyloxyethylene), 60% syndiotactic poly(formyloxyethylene), poly[4-(sec-butoxymethyl) styrene], poly(4-butoxystyrene), and blends thereof.

6. The coating of claim 1, wherein the polymer in the second region has a melting temperature above about 50° C.

7. A topcoat for an implantable medical device, comprising a first phase comprising a polymer, and a second phase comprising a material immiscible with the polymer, the material having a melting temperature within the range between about 32° C. and 40° C., wherein when the body temperature of a patient in which the implantable medical device comprising the topcoat is implanted rises to a temperature above the patient's normal body temperature, the morphology of the topcoat changes so as to change the release rate of a drug in a coating under the topcoat.

8. The topcoat of claim 7, wherein the implantable medical device is a stent.

9. The topcoat of claim 7, wherein the material has a melting temperature of about 37° C.

10. The topcoat of claim 7, wherein the polymer comprises an acrylic polymer, a non-acrylic polymer, or blends thereof.

11. The topcoat of claim 10, wherein the non-acrylic polymer is selected from the group consisting of poly(2-cyclohexylethylethylene), atactic poly(isopropylethylene), poly(1,1,2-trimethylethylene), poly(4,4 dimethylpentylethylene), poly(2,2,2-trifluoroethoxytrifluoroethylene), poly(4-methoxybenzoylethylene), poly(3,4-dimethoxybenzoylethylene), poly(vinyl fluoride), poly(cyclopentanoyloxyethylene), 60% syndiotactic poly(formyloxyethylene), poly[4-(sec-butoxymethyl) styrene], poly(4-butoxystyrene), and blends thereof.

12. The topcoat of claim 7, wherein the drug is an anti-inflammatory drug.

13. The coating of claim 4, wherein the acrylic polymer is selected from the group consisting of poly(tert-butyl acrylate), poly[3-chloro-2,2-bis(chloromethyl) propyl acrylate], poly(cyanobenzyl acrylate), poly(2-methoxycarbonylphenyl acrylate), poly(3-methoxycarbonylphenyl acrylate), poly(4-ethoxycarbonylphenyl acrylate), poly(hexadecyl acrylate), poly(3-dimethylaminophenyl acrylate), polyp-tolyl acrylate), poly(n-butyl acrylamide), poly(iso-decyl acrylamide), poly(octafluoropentyl methacrylate), poly(3,3-dimethylbutyl methacrylate), isotactic poly(methyl methacrylate), poly(n-propyl methacrylate), isotactic poly(ethyl chloroacrylate), poly(ethyl fluoromethacrylate), and blends thereof.

14. The coating of claim 4, wherein the acrylic polymer is of the formula

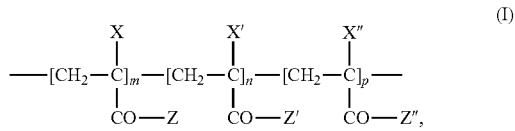

wherein:
X, X', and X" is each, independently, a hydrogen atom or an alkyl group;
Z, Z', and Z" is each, independently, a substituted or unsubstituted amino group or an alkoxy group OR, OR', and OR", where R, R' and R" is each, independently, a $C_1$ to $C_{12}$ straight chained or branched aliphatic radical; and
each of m, n, and p is an integer, where m>0, n≧0, and p≧0.

15. The topcoat of claim 10, wherein the acrylic polymer is selected from the group consisting of poly(tert-butyl acrylate), poly[3-chloro-2,2-bis(chloromethyl) propyl acrylate], poly(cyanobenzyl acrylate), poly(2-methoxycarbonylphenyl acrylate), poly(3-methoxycarbonylphenyl acrylate), poly(4-ethoxycarbonylphenyl acrylate), poly(hexadecyl acrylate), poly(3-dimethylaminophenyl acrylate), polyp-tolyl acrylate), poly(n-butyl acrylamide), poly(iso-decyl acrylamide), poly(octafluoropentyl methacrylate), poly(3,3-dimethylbutyl methacrylate), isotactic poly(methyl methacrylate), poly(n-propyl methacrylate), isotactic poly(ethyl chloroacrylate), poly(ethyl fluoromethacrylate), and blends thereof.

16. The topcoat of claim 10, wherein the acrylic polymer is of the formula

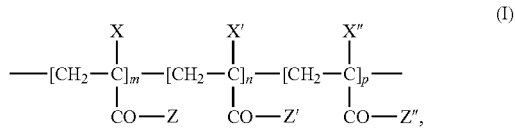

wherein:
X, X', and X" is each, independently, a hydrogen atom or an alkyl group;
Z, Z', and Z" is each, independently, a substituted or unsubstituted amino group or an alkoxy group OR, OR', and OR", where R, R' and R" is each, independently, a $C_1$ to $C_{12}$ straight chained or branched aliphatic radical; and
each of m, n, and p is an integer, where m>0, n≧0, and p≧0.

17. The coating of claim 1, wherein the material is selected from the group consisting of 1-tetradecanol, Vegetable wax, Cocoa butter, and Triglyceride (stearin-dipalmityl).

18. The topcoat of claim 7, wherein the material is selected from the group consisting of 1-tetradecanol, Vegetable wax, Cocoa butter, and Triglyceride (stearin-dipalmityl).

* * * * *